(12) United States Patent
Eng (10) Patent No.: US 6,841,505 B2
(45) Date of Patent: Jan. 11, 2005

(54) TITANIUM-ZIRCONIUM CATALYST COMPOSITIONS AND USE THEREOF

(75) Inventor: John H. Eng, Wilmington, DE (US)

(73) Assignee: E..I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/269,363

(22) Filed: Oct. 11, 2002

(65) Prior Publication Data

US 2004/0018938 A1 Jan. 29, 2004

Related U.S. Application Data

(60) Provisional application No. 60/398,675, filed on Jul. 26, 2002.

(51) Int. Cl.[7] .................................................. B01J 31/00
(52) U.S. Cl. ........................ 502/150; 528/279; 560/98; 525/10
(58) Field of Search .......................... 502/150; 560/98; 528/279; 525/10

(56) References Cited

U.S. PATENT DOCUMENTS

| | | |
|---|---|---|
| 3,056,818 A | 10/1962 | Werber |
| 3,326,965 A | 6/1967 | Schultheis et al. |
| 5,120,822 A | 6/1992 | Hoeschele et al. |
| 5,268,503 A | 12/1993 | Karasawa et al. |
| 5,684,116 A | 11/1997 | Martl et al. |
| 5,840,957 A | 11/1998 | Kurian et al. |
| 5,866,710 A * | 2/1999 | Ridland et al. ................ 560/98 |
| 5,981,690 A | 11/1999 | Lustig et al. |
| 6,043,335 A | 3/2000 | Banach et al. |
| 6,075,115 A | 6/2000 | Putzig et al. |
| 6,166,170 A | 12/2000 | Putzig |
| 6,255,441 B1 * | 7/2001 | Putzig et al. ................ 528/271 |
| 6,255,442 B1 | 7/2001 | Kurian et al. |
| 6,281,325 B1 | 8/2001 | Kurian et al. |
| 6,335,421 B1 | 1/2002 | Kurian et al. |
| 6,353,062 B1 | 3/2002 | Giardino et al. |
| 6,372,929 B1 * | 4/2002 | Ridland et al. ................ 556/24 |
| 6,407,269 B2 | 6/2002 | Kaita et al. |
| 6,512,080 B2 | 1/2003 | Kelsey et al. |
| 6,541,411 B2 * | 4/2003 | Hoffmann et al. .......... 502/108 |
| 2002/0032302 A1 | 3/2002 | Scardino et al. |

FOREIGN PATENT DOCUMENTS

| | | |
|---|---|---|
| GB | 1 437 897 | 6/1976 |
| JP | 52-136294 | 11/1977 |
| JP | 1993339392 A | 7/1978 |
| JP | 53-85891 | 12/1993 |
| JP | 1994234701 A | 8/1994 |
| WO | WO 99/28033 | 6/1999 |
| WO | WO 99/54379 | 10/1999 |
| WO | WO 00/46271 | 8/2000 |
| WO | WO 00/71252 A1 | 11/2000 |
| WO | WO 01/56694 A1 | 8/2001 |
| WO | WO 01/58981 A1 | 8/2001 |

OTHER PUBLICATIONS

H. L. Traub, "Synthese und textilchemische Eigenschaften de Poly–Trimethyleneterephthalats", *Dissertaion Universitat Stuttgart*, (1994) (English Translation).

(List continued on next page.)

*Primary Examiner*—Mark L. Bell
*Assistant Examiner*—Jennine M. Brown
(74) *Attorney, Agent, or Firm*—Mark D. Kuller (57) ABSTRACT

A catalyst composition prepared from (a) titanium tetrahydrocarbyloxide, (b) zirconium tetrahydrocarbyloxide, and (c) tetraalkyl ammonium hydroxide, wherein the molar ratio of Zr:Ti is from about 0.02:1 to about 5:1 and the molar ratio of TAAH:(Ti+Zr) is from about 0.05:1 to about 2:1.

25 Claims, 2 Drawing Sheets

OTHER PUBLICATIONS

A. Greiner, "Study of Mixtures of Titanium– and Zirconium Alkoxides as Catalysts in Polycondensation of PET", Institute of Man–Made Fibers, (1999).

DuPont™ Tyzor® Organic Titanates, General Brochure, E. I. du Pont de Nemours and Company (Copyright Dupont 2001).

English Abstract FR 83866 (Martin–Marietta Corp.) Oct. 30, 1964, "Esterification of terephthalic and isophthalic acids" (HCAPLUS, Copyright 2002 ACS).

International Search Report, date of mailing Dec. 24, 2003.

* cited by examiner

TITANIUM-ZIRCONIUM CATALYST COMPOSITIONS AND USE THEREOF

RELATED APPLICATIONS

This application claims priority from U.S. Provisional Patent Application Ser. No. 60/398,675, filed Jul. 26, 2002, which is hereby incorporated by reference.

FIELD OF THE INVENTION

The present invention relates to a catalyst composition comprising a titanium compound, and to a process for using the composition in, for example, esterification, transesterification, or polymerization reactions.

TECHNICAL BACKGROUND

All the documents cited herein are incorporated by reference.

Polyesters such as, for example, poly(ethylene terephthalate) ("PET") and poly(tetramethylene terephthalate) ("PBT", also known as "poly(butylene terephthalate)"), generally referred to as "polyalkylene terephthalates", are a class of important industrial polymers. Recently, poly(trimethylene terephthalate) ("PTT" or "3GT"), also called polypropylene terephthalate, has achieved commercial importance because of its elasticity, as measured, by its elastic recovery and resilience. These polyesters are widely used in shaped articles including thermoplastic fibers, films, and molding applications.

Polyalkylene terephthalates can be produced by transesterification of a dialkyl terephthalate ester with a glycol or by direct esterification of terephthalic acid with the selected glycol, followed by polycondensation. Catalysts can be used to catalyze the esterification or transesterification, and catalysts are generally used in polycondensation.

Catalysts known in the art include titanium and zirconium compounds. Organo titanium and organo zirconium compounds are well known catalysts for esterification, transesterification and polycondensation. Organic titanates, such as tetraisopropyl and tetra n-butyl titanates, are known to be effective polycondensation catalysts for preparing polyalkylene terephthalates in general, and frequently are the catalyst of choice. Use of such catalysts for polyester production results in formation of organic titanium compounds which impart color to the polymer. Thus, increasing catalyst concentration to increase rate in a titanium-catalyzed esterification, transesterification, or polycondensation can negatively impact color.

Combinations of titanium and zirconium compounds as catalysts to effect polyester production are known. For instance, U.S. Pat. No. 5,120,822 discloses a process to prepare polyesters containing a non-vicinal aliphatic diol, e.g., 1,4-butanediol or 1,3-propanediol with a dicarboxylic acid or equivalent in the presence of a titanate and zirconate catalyst. The ratio of Ti atoms to Zr atoms is 1.3:1 to 9:1. U.S. Pat. No. 6,043,335 and WO 00/46271 disclose a combination of titanium, zirconium, and phosphorus compounds for preparing a polyester, wherein the ratio of Zr:Ti is 1–5:1 and P compound:Ti is 1–25:1. A. Greiner, "Study of Mixtures of Titanium- and Zirconium Alkoxides as Catalysts in Polycondensation of PET" (Institute of Man-Made Fibers, Denkendorf, 1999) describes experiments conducted using mixtures of titanium- and zirconium alkoxide catalysts, such as tetra-n-butyl-titanate and Tyzor® NPZ tetra-n-propyl-zirconate (E. I. du Pont de Nemours and Company, Wilmington, Del., hereinafter "DuPont") catalysts.

U.S. Pat. No. 5,981,690 discloses a process to prepare a poly(alkylene) terephthalate using a combination of titanium and zirconium complexes and an organo phosphorous compound.

U.S. Pat. No. 6,372,929 describes an organometallic compound for use as a catalyst for the preparation of polyesters comprising the reaction product of an orthoester or condensed orthoester of titanium, zirconium or aluminum, an alcohol containing at least two hydroxyl groups, an organophosphorus compound containing at least one P—OH group and a base. The base is generally an inorganic base such as sodium hydroxide, but organic bases, such as tetrabutyl ammonium hydroxide are mentioned.

WO 01/56694 describes esterification catalysts which are a complex of a first metal selected from the group consisting of titanium or zirconium, a second metal selected from the group consisting of germanium, antimony or tin, and a carboxylic acid. Suitable sources of the first metal include tetraisopropoxy titanium, tetra-n-butoxy titanium, tetra-n-propoxy zirconium and tetra-n-butoxy zirconium. Examples of carboxylic acids are acetic, oxalic, capric, lauric, lactic, citric, malic and tartaric acids. Solubilizing compounds can be used and include dihydric alcohols, such as 1,2-ethanediol, 1,3-propanediol and 1,4-butanediol. A base can also be used in preparing the complex. Suitable bases are disclosed to include inorganic bases, such as sodium hydroxide, and organic bases, such as tetrabutyl ammonium hydroxide.

WO 00/71252 describes catalysts which comprises: (a) an organometallic compound which is the reaction product of an orthoester or condensed orthoester of at least one metal selected from titanium, zirconium or aluminum, an alcohol containing at least two hydroxyl groups, and an organophosphorus compound containing at least one P—OH group, and (b) at least one compound of germanium, antimony or tin. Component (a) can also be prepared with a 2-hydroxy carboxylic acid. This document states that reference to titanium, zirconium or aluminum orthoester or condensed orthoester is intended to include orthoesters or condensed orthoesters of more than one metal, e.g., to a mixture of titanium and zirconium orthoesters. In a preferred embodiment the organometallic compound (a) includes a base. Suitable bases are disclosed to include inorganic bases, such as sodium hydroxide, and organic bases, such as tetrabutyl ammonium hydroxide. The catalyst is stated to be useful in preparing polyesters such as poly(ethylene terephthalate), poly(trimethylene terephthalate) and poly(tetramethylene terephthalate).

Present catalyst for preparing polyesters still have drawbacks. There is a need for a new catalyst that is more efficient. There is also a need for an efficient, stable catalyst that produces a polymer with reduced color. These and other objectives of this invention are described below.

SUMMARY OF THE INVENTION

The invention is directed to a catalyst composition prepared from (a) titanium tetrahydrocarbyloxide, (b) zirconium tetrahydrocarbyloxide, and (c) tetraalkyl ammonium hydroxide ("TAAH"), wherein the molar ratio of Zr:Ti is from about 0.02:1 to about 5:1 and the molar ratio of TAAH:(Ti+Zr) is from about 0.05:1 to about 2:1.

Preferably the titanium tetrahydrocarbyloxide is tetraalkyl titanate.

Preferably the zirconium tetrahydrocarbyloxide is tetraalkyl zirconate.

The invention is further directed to a catalyst composition consisting essentially of the product of mixing (a) tetraalkyl titanate, (b) tetraalkyl zirconate, and (c) tetraalkyl ammonium hydroxide, wherein the molar ratio of Zr:Ti is from about 0.02:1 to about 5:1 and the molar ratio of TAAH:(Ti+Zr) is from about 0.05:1 to about 2:1. The product can be prepared my adding (a), (b) and (c) in any order.

Preferably the catalyst composition does not contain phosphorus or a phosphorus compound.

The invention is also directed to a catalyst composition prepared from (a) tetraalkyl titanate, (b) tetraalkyl zirconate, and (c) tetraalkyl ammonium hydroxide, which does not contain phosphorus or a phosphorus compound, wherein the molar ratio of Zr:Ti is from about 0.02:1 to about 5:1 and the molar ratio of TAAH:(Ti+Zr) is from about 0.05:1 to about 2:1.

The molar ratio of titanium tetrahydrocarbyloxides:zirconium tetrahydrocarbyloxides is calculated based on the molar ratio of Zr:Ti, is preferably at least about 0.1:1, and is preferably up to about 3:1, more preferably up to about 1:1. Thus, preferred ranges include 0.1:1 to 3:1 and 0.1:1 to 1:1.

The molar ratio of tetraalkyl ammonium hydroxide to titanium tetrahydrocarbyloxides and zirconium tetrahydrocarbyloxides is calculated based on the molar ratio of TAAH:(Ti+Zr), is preferably at least about 0.1, and is preferably up to about 1:1, more preferably up to about 0.5, with about 0.3 being most preferred. Thus, preferred ranges of TAAH:(Ti+Zr) include 0.05:1 to 1:1 and 0.1:1 to 0.5:1.

Preferably the tetraalkyl titanate is selected from those having the general formula $Ti(OR)_4$ where each R is independently selected from the group consisting of an alkyl radical, a cycloalkyl radical, an aralkyl hydrocarbon radical containing from 1 to 30 carbon atoms, and combinations thereof. More preferably the tetraalkyl titanate is selected from the group consisting of titanium tetraethoxide, titanium tetrapropoxide, titanium tetrahexoxide, titanium tetra 2-ethylhexoxide, titanium tetraoctoxide, titanium tetraisopropoxide and titanium tetra-n-butoxide and combinations thereof.

Preferably the tetraalkyl zirconate is selected from tetraalkyl zirconates having the general formula $Zr(OR^1)_4$ where each $R^1$ can be the same or different and is a hydrocarbyl radical having 1 to about 10 carbon atoms per radical, and combinations thereof. More preferably the tetraalkyl zirconate is selected from the group consisting of tetra n-propyl zirconate, tetra n-butyl zirconate, and combinations thereof.

Preferably the tetraalkyl ammonium hydroxide is selected from the group consisting of tetraalkyl ammonium hydroxides with alkyl groups containing 1–20 carbon atoms, more preferably 1–10 carbon atoms, which can be the same or different, and combinations thereof. Even more preferably the tetraalkyl ammonium hydroxide selected from the group consisting of tetra methyl, ethyl, propyl and butyl ammonium hydroxide, choline hydroxide, (trimethyl(2-hydroxyethyl)ammonium hydroxide), benzyltrimethyl ammonium hydroxide, and combinations thereof.

In one preferred embodiment, the tetraalkyl titanate is selected from those having the general formula $Ti(OR)_4$ where each R is independently selected from alkyl radicals with 2 to 12 carbon atoms per radical and combinations thereof; the tetraalkyl zirconate is selected from the group having the general formula $Zr(OR^1)_4$ where each $R^1$ is independently selected from an alkyl radical having 1 to 10 carbon atoms and combinations thereof; and the tetraalkyl ammonium hydroxide is selected from the group consisting of tetraalkyl ammonium hydroxides with alkyl groups containing 1–10 carbon atoms, which can be the same or different, and mixtures thereof, and wherein the molar ratio of Zr:Ti is 0.1:1 to 1:1 and the molar ratio of TAAH:(Ti+Zr) is 0.1:1 to 0.5:1.

In addition, the invention is directed to a catalyst mixture comprising the catalyst composition described above and glycol. Preferably the glycol is a $C_2$ to $C_{12}$ glycol, and more preferably the glycol is selected from the group consisting of ethylene glycol, 1,2-propanediol, 1,3-propanediol and 1,4-butanediol, and mixtures thereof.

The invention is also directed to a process of producing a polyester comprising esterifying or transesterifying (a) organic acid, or ester or salt of an organic acid, and (b) alcohol to form an intermediate reaction product and, polycondensing the intermediate reaction product to form polyester, wherein the catalyst composition catalyzes the esterifying, transesterifying or polycondensing The polyester is preferably poly(trimethylene terephthalate). The alcohol is preferably a diol, such as 1,3-propanediol. The intermediate reaction product is polyester oligomers, preferably having an average degree of polymerization of about 2 to about 8. By the "catalyst composition catalyzes the esterifying, transesterifying or polycondensing" it should be understood that the catalyst composition can be used to catalyze (a) esterifying or transesterifying and/or (b) polycondensing, and can be added before or during either of these steps, and can be added once or at many points during any or both steps.

The catalyst compositions of this invention are useful as esterification, transesterification, or polycondensation catalysts. The invention provides a stable catalyst that is more efficient than tetra isopropyl titanate per mass of Ti and other catalysts known in the art, that produces polyesters with low color. Most notably, polyesters with low color can be prepared without adding phosphorus or phosphorus containing compounds that are known to reduce color but reduce overall catalyst activity.

BRIEF DESCRIPTION OF THE DRAWINGS

FIG. 1 shows the temperature profiles during transesterification in Example 8 and Comparative Example 7. The earlier rise in temperature at the top of the column in Example 8 versus Comparative Example 7 indicates that methanol is being generated earlier with the catalyst of this invention than with a tetra isopropyl titanate catalyst at the same level of Ti. Because of the earlier production of methanol, the overall time for transesterification is reduced when using the catalyst of this invention.

DETAILED DESCRIPTION OF THE INVENTION

All the documents cited herein are incorporated by reference.

Reference herein to a compound should be understood to mean a single compound or blends or mixtures of such compounds. For instance, "polyester" means one or more polyesters. Thus, for instance, if applicant refers to a composition containing x mole % of a polyester, the composition may comprise x mole % of one polyester or x mole % total of different polyesters.

The invention is directed to a catalyst composition prepared from (a) titanium tetrahydrocarbyloxides, (b) zirconium tetrahydrocarbyloxides, and (c) tetraalkyl ammonium hydroxide.

The preferred titanium tetrahydrocarbyloxides are tetraalkyl titanates (also known as "titanium tetraalkoxide"). The preferred titanium tetrahydrocarbyloxides include those expressed by the general formula $Ti(OR)_4$ where each R is independently (i.e., each R can be the same or different) selected from the group consisting of an alkyl radical, a cycloalkyl radical, an aralkyl hydrocarbon radical, and combinations of two or more thereof. Each radical can contain from 1 to about 30, preferably 2 to about 18, and most preferably 2 to 12 carbon atoms per radical and each R can be the same or different. Titanium tetrahydrocarbyloxides in which the hydrocarbyl group contains from 2 to about 12 carbon atoms per radical which is a linear or branched alkyl radical are most preferred because they are relatively inexpensive, more readily available, and effective in forming the solution. Preferred titanium tetrahydrocarbyloxides include titanium tetraethoxide, titanium tetrapropoxide, titanium tetrahexoxide, titanium tetra 2-ethylhexoxide, titanium tetraoctoxide, and combinations of any two or more thereof. Most preferred are titanium tetraisopropoxide and titanium tetra-n-butoxide.

The presence of a halide, or of other active substituent, in the R group generally is avoided since such substituents can interfere with catalytic reactions or form undesired by-products, which can contaminate the polymer when the titanium compound is used for producing a polymer. It is preferred that the each R group is identical to facilitate synthesis of the organic titanate; however, they do not have to be the same. In some cases two or more R groups can be from a common compound chemically bonded together other than at the titanium atom (i.e., multidentate ligands such as triethanolamine, citric acid, lactic acid, malic acid, tartaric acid, hydroxyglycine, a salt of the acid, and combinations of two or more thereof).

Examples of commercially available organic titanium compounds include, but are not limited to, TYZOR® TPT and TYZOR® TnBT (tetra isopropyl titanate and tetra n-butyl titanate, respectively), available from DuPont.

The preferred zirconium tetrahydrocarbyloxides are tetraalkyl zirconates. The preferred zirconium tetrahydrocarbyloxides include those expressed by the general formula $Zr(OR^1)_4$ where each $R^1$ can be the same or different and is a hydrocarbyl radical having 1 to about 10, preferably 1 to about 8, and most preferably 1 to 5 carbon atoms per radical. The presently preferred $R^1$ is an alkyl radical, either branched or straight chain. Examples of suitable organic zirconium compounds include, but are not limited to, tetra n-propyl zirconate, tetra n-butyl zirconate, and combinations of two or more thereof. Tetra n-propyl zirconate and tetra n-butyl zirconate are preferred organic zirconates, and are commercially available from DuPont under the "TYZOR" trademark.

The invention is prepared using tetraalkyl ammonium hydroxide, which is a base. Preferred are tetraalkyl ammonium hydroxides with alkyl groups containing 1–20 carbon atoms, more preferably 1–10 carbon atoms, and most preferably 1–6 carbon atoms. Examples include choline hydroxide, (trimethyl(2-hydroxyethyl)ammonium hydroxide) and benzyltrimethyl ammonium hydroxide. Preferred are tetramethyl, tetraethyl, tetrapropyl and tetrabutyl ammonium hydroxide and mixtures thereof.

Any solvent that can produce a suitable mixture with the catalyst composition can be used in the present invention. The presently preferred solvent is an alcohol having the formula of $R^1(OH)_n$, an alkylene glycol of the formula $(HO)_nA(OH)_n$, a polyalkylene glycol or alkoxylated alcohol having the formula of $R^1O[CH_2CH(R^1)O]_nH$, or combinations of two or more thereof in which each $R^1$ is the same as that disclosed above. A is an alkylene group and can have 2 to about 10, preferably 2 to about 7, and most preferably 2 to 4 carbon atoms per molecule. Each n can be the same or different and is independently a number in the range of from 1 to about 10, preferably 1 to about 7, and most preferably 1 to 5. Examples of suitable solvents include, but are not limited to, ethanol, propanol, isopropanol, butanol, ethylene glycol, propylene glycol, isopropylene glycol, butylene glycol, 1-methyl propylene glycol, pentylene glycol, diethylene glycol, triethylene glycol, cyclohexyl-bis-1,4-dimethanol diethylene glycol monomethyl ether, triethylene glycol monomethylether, 2-ethyl hexanol, and combinations of two or more thereof. The presently preferred solvent is the glycol corresponding to the ester being produced, e.g., ethylene glycol for poly(ethylene terephthalate), 1,3-propanediol for poly(trimethylene terephthalate) and 1,4-butanediol for poly(tetramethylene terephthalate).

The catalyst can be prepared by adding titanium tetrahydrocarbyloxides, zirconium tetrahydrocarbyloxides, tetraalkyl ammonium hydroxide and solvent in any order. Mixing can be started at any time. Preferably titanium tetrahydrocarbyloxides is added to zirconium tetrahydrocarbyloxides, and they are mixed. Then, the tetraalkyl ammonium hydroxide is added with mixing, which results in a slight exotherm. Next, the solvent (e.g., ethylene glycol, 1,3-propanediol, 1,4-propanediol, etc.) is added to make a solution. Following this procedure with the invention, e.g., with tetra-isopropyl titanate, tetrapropyl zirconate, tetramethyl ammonium hydroxide, and 1,3-propanediol, it is possible to prepare a clear liquid, whereas when tetra-isopropyl titanate and 1,3-propanediol are used by themselves a chunky mixture (with solids) results. Similar benefits can result with other glycols.

The molar ratio of titanium tetrahydrocarbyloxides:zirconium tetrahydrocarbyloxides, calculated based on the molar ratio of Zr:Ti therein, is from about 0.02:1 to about 5:1, is preferably at least about 0.1:1, and is preferably up to about 3:1, more preferably up to about 1:1.

The molar ratio of tetraalkyl ammonium hydroxide to titanium tetrahydrocarbyloxides and zirconium tetrahydrocarbyloxides, calculated as TAAH:(Ti+Zr) is from about 0.05:1 to about 2:1, is preferably at least about 0.1:1, and is preferably up to about 1:1, more preferably up to about 0.5:1, with about 0.3:1 being most preferred.

Preferably the catalyst composition is mixed with the solvent so that the titanium weight ratio in the solution is less than about 10 weight %, more preferably less than about 5 weight %, and even more preferably less than 1 weight %, and it is preferably at least about 0.1 weight %, more preferably at least about 0.5 weight %.

Preferably the catalyst composition is added in an amount of about 25 to about 2,000 ppm Ti, based on the weight of the final polyester. For making poly(trimethylene terephthalate), preferred is about 25 to about 200 ppm Ti, more preferably 25 to 100 ppm Ti, based on the resulting poly(trimethylene terephthalate). The catalyst can be added before or during esterification or transesterification, and/or before or during polycondensation. Single or multiple insertions can be used. In one preferred embodiment, it is added prior to esterification or transesterification, and, optionally, at additional points later or downstream in the process. In another preferred embodiment, it is added prior to polycondensation.

Phosphorus and phosphorus containing compounds are stabilizers and improve polymer color, but they are known to reduce the activity of titanium catalysts. Therefore, there is a trade-off between stabilization and color, and reduced activity. The catalyst of the invention can contain phosphorus or phosphorus containing compound(s), particularly in an amount suitable to stabilize the system or improve polyester color. However, the catalyst composition (as well as the catalyst mixture, reactants and polyesters) preferably does not contain phosphorus or phosphorus compound(s) in an amount that significantly reduces catalyst activity in preparing polyester. In fact, the catalyst composition (as well as the catalyst mixture, reactants and polyesters) preferably do not contain any phosphorus or phosphorus compound(s).

It is noted that $TiO_2$ can contain phosphorus, for instance when coated with a phosphorus containing compound or when a phosphorus-containing compound is used to aid dispersion of $TiO_2$, and that $TiO_2$ can be added as part of the catalyst mixture. Thus, in another preferred embodiment, the catalyst mixture and/or the reactants or products do not contain phosphorus/phosphorus compound(s) added except those resulting from addition of $TiO_2$.

The catalyst compositions of this invention are useful for preparing esters and polyesters. That is, they are useful in esterification, transesterification and polycondensation. It can be used in one or more steps in making polyesters.

One preferred class of polymers is polyesters. By "polyester" or "a polyester", applicant is referring to a single polyester, and/or to blends or mixtures of polyesters. The preferred polyesters are polyalkylene terephthalates, polyalkylene naphthalates and polyalkylene isophthalates, and polyalkylene terephthalates are most preferred. More preferred are poly(ethylene terephthalate)s, poly(trimethylene terephthalate)s and poly(tetramethylene terephthalate)s, and poly(trimethylene terephthalate)s are most preferred.

In the absence of an indication to the contrary, a reference to polyester is intended to include reference to copolyesters. For instance, reference to "polyalkylene terephthalate" is meant also to encompass copolyesters, i.e., polyesters made using 3 or more reactants, each having two ester forming groups. For example, a copoly(ethylene terephthalate) can be used in which the comonomer used to make the copolyester is selected from the group consisting of linear, cyclic, and branched aliphatic dicarboxylic acids having 4 to 12 carbon atoms (for example butanedioic acid, pentanedioic acid, hexanedioic acid, dodecanedioic acid, and 1,4-cyclohexanedicarboxylic acid); aromatic dicarboxylic acids other than terephthalic acid and having 8–14 carbon atoms (for example isophthalic acid and 2,6-naphthalenedicarboxylic acid); and from linear, cyclic, and branched aliphatic diols having 3–8 carbon atoms (for example 1,3-propanediol, 1,2-propanediol, 1,4-butanediol, 3-methyl-1,5-pentanediol, 2,2-dimethyl-1,3-propanediol, 2-methyl-1,3-propanediol, and 1,4-cyclohexanediol); and aliphatic and aromatic ether glycols having 4–10 carbon atoms (for example, hydroquinone bis(2-hydroxyethyl) ether, or a poly(ethylene ether) glycol having a molecular weight below about 460, including diethylene ether glycol). The comonomer typically can be present in the copolyester at levels in the range of about 0.5 to about 15 mole %. Isophthalic acid, pentanedioic acid, hexanedioic acid, 1,3-propane diol, and 1,4-butanediol are preferred because they are readily commercially available and inexpensive.

Copoly(trimethylene terephthalate) made from 1,3-propanediol can also be used, in which case the comonomer (s) can be selected from the above list (except the aliphatic diols having 2–8 carbon atoms may be used and ethylene glycol should replace 1,3-propanediol in the list). The copolyester(s) can contain minor amounts of other comonomers, and such comonomers are usually selected so that they do not have a significant adverse affect on the amount of fiber crimp (in the case of a spontaneously crimpable polyester bicomponent fibers) or on other properties. Very small amounts of trifunctional comonomers, for example trimellitic acid, can be incorporated for viscosity control.

The polyester (e.g., poly(trimethylene terephthalate)) can contain minor amounts of other comonomers, and such comonomers are usually selected so that they do not have any significant adverse affect on properties. Such other comonomers include 5-sodium-sulfoisophthalate, for example, at a level in the range of about 0.2 to about 5 mole %. Very small amounts of trifunctional comonomers, for example trimellitic acid, can be incorporated for viscosity control.

The preferred poly(trimethylene terephthalate)s contain at least 85 mole %, more preferably at least 90 mole %, even more preferably at least 95 or at least 98 mole %, and most preferably about 100 mole %, poly(trimethylene terephthalate) polymer.

The intrinsic viscosity of the preferred poly(trimethylene terephthalate)s of the invention is at least about 0.70 dl/g, preferably at least about 0.80 dl/g, more preferably at least about 0.90 dl/g and most preferably at least about 1.0 dl/g. The intrinsic viscosity of the polyester composition of the invention are preferably up to about 2.0 dl/g, more preferably up to 1.5 dl/g, and most preferably up to about 1.2 dl/g.

The polymers can be made using conventional techniques. Poly(trimethylene terephthalate)s can be manufactured by batch, semi-batch, continuous and other known techniques, such as by the processes described in U.S. Pat. Nos. 5,015,789, 5,276,201, 5,284,979, 5,334,778, 5,364,984, 5,364,987, 5,391,263, 5,434,239, 5,510454, 5,504,122, 5,532,333, 5,532,404, 5,540,868, 5,633,018, 5,633,362, 5,677,415, 5,686,276, 5,710,315, 5,714,262, 5,730,913, 5,763,104, 5,774,074, 5,786,443, 5,811,496, 5,821,092, 5,830,982, 5,840,957, 5,856,423, 5,962,745, 5,990,265, 6,235,948,6,245,844,6,255,442, 6,277,289. 6,281,325, 6,312,805, 6,325,945, 6,326,456, 6,331,264, 6,335,421, 6,350,895, and 6,353,062, EP 998 440, WO 98/57913, 00/14041, WO 01/58981 and 01/58982, H. L. Traub, "Synthese und textilchemische Eigenschaften des Poly-Trimethyleneterephthalats", Dissertation Universitat Stuttgart (1994), S. Schauhoff, "New Developments in the Production of Poly(trimethylene terephthalate) (PTT)", Man-Made Fiber Year Book (September 1996), and U.S. patent application Ser. No. 10/057,497 (now U.S. Pat. No. 6.538.076), all of which are incorporated herein by reference. Continuous processes such as described by U.S. Pat. No. 6,353,062, U.S. patent application Ser. Nos. 09/502,642, filed Feb. 11, 2000 (abandoned), 10/057,497, filed May 22, 2001 (now U.S. Pat. No. 6.538.076), WO 01/58981 and 0 1/58982, all of which are incorporated herein by reference, are most preferred.

Additives, including delusterants, stabilizers, viscosity boosters, optical brighteners, pigments, and antioxidants, can be used. $TiO_2$ or other pigments can be added, such as described in U.S. Pat. Nos. 3,671,379, 5,798,433 and 5,340,909, EP 699 700 and 847 960, and WO 00/26301, which are incorporated herein by reference.

The compositions of this invention are useful for many purposes including preparing shaped articles, e.g., fibers, fabrics, carpets, films, film layers, parts, bottles, etc., and methods of making and using such compositions and articles are well known. By "fibers", reference is made to items recognized in the art as fibers, such as continuous filaments (bulked continuous filaments, partially oriented yarns, spun drawn yarns, draw textured yarns, etc.), staple, and other chopped fibers. The fibers may be monocomponent (sometimes also referred to as "homofibers"), or bicomponent or other multicomponent fibers, including sheath-core, eccentric sheath-core, and side-by-side fibers, and yarns made therefrom. Fabrics include knitted, woven and nonwoven fabrics.

EXAMPLES

The following examples are presented for the purpose of illustrating the invention, and are not intended to be limiting. All parts, percentages, etc., are by weight unless otherwise indicated.

Color & Brightness

The color and brightness of batch poly(trimethylene terephthalate) samples were determined using a Varian (Palo Alto Calif.) Cary 5 UV/Vis/NIR spectrophotometer with a diffuse reflectance accessory. The reflectance data was processed using the color analysis application within Grams/32 software with an observer angle of 2 degrees and a CIE A light source. Hunter L*, a*, and b* were calculated. The L* coordinate indicated brightness, where 0 was black and 100 was white. The a* value could be positive or negative, where positive values were indicative of red color and negative indicated green. The b* value was similar, where positive values indicated yellow and negative values indicated blue.

The color and brightness of continuously prepared poly (trimethylene terephthalate) samples (Comparative Examples 9 through Example 14) were measured using a Hunterlab LabScan XE with DP-9000 system (Reston, Va.). The DP-9000 performs integration of reflectance values over the visible spectrum to arrive at CIE tristimulus X, Y and Z values as outlined in publication CIE 15.2 and ASTM method E308. The tristimulus X, Y and Z values are used to calculate Hunter L, a, and b values. Hunter L, a, and b colors are related to color in the same manner as Hunter L*, a*, and b*, but have higher values due to their different conversions.

Intrinsic Viscosity (IV)

Intrinsic viscosities were measured using a Viscotek Forced Flow Viscometer model Y-900. Polymers were dissolved in 50/50 w/w trifluoroacetic acid/methylene chloride at a 0.4% (wt/vol) concentration and were tested at 19° C. The intrinsic viscosities determined by this method are equivalent to values determined using Goodyear Method R-103b".

Relative Viscosity

Relative viscosity is an indicator of molecular weight. Relative viscosity, often referred to as "LRV," is the ratio of the viscosity of a solution of 4.75 grams of poly (trimethylene terephthalate) in 100 grams of solution to the viscosity of the solvent itself. The solvent used herein for measuring relative viscosity is hexafluoroisopropanol containing 100 ppm sulfuric acid, and the measurements are made at 25° C.

Example 1

The effectiveness of various catalysts for esterification and transesterification was evaluated using reactions comprised of mixtures of methyl benzoate ("MB", Aldrich), benzoic acid ("BA", Aldrich), catalyst and 1,3-propanediol ("3G"). The reaction of methyl benzoate with 3G is an ester exchange reaction, similar to the reaction of dimethyl terephthalate ("DMT") with a glycol (transesterification) or polycondensation reactions to extend chain length. The reaction of benzoic acid with 3G is similar to the reaction of terephthalic acid ("TPA") or isophthalic acid ("IPA") with 3G.

Solution A was prepared by adding 0.0201 g of tetraisopropyl titanate catalyst (Tyzor® TPT tetraisopropyl titanate from DuPont) ("TPT") to 104.68 g of 3G and mixing well to obtain a homogeneous mixture of Ti in 3G. Solution B was prepared by mixing 0.0225 g of zirconium propoxide (Tyzor® NPZ 70% zirconium propoxide in n-propanol from DuPont) ("NPZ") in 137.20 g of 3G. Solution C was prepared by mixing 0.1259 g of 1 M tetrabutyl ammonium hydroxide in methanol ("TBAH", Aldrich) in 118.33 g of 3G. Each of the solutions was clear before use.

Controlled amounts of MB, BA, 3G in catalyst solutions A, B and C, or without catalyst, were added to separate 2 mL glass vials. The vials were then capped and placed in a temperature-controlled block heater to ensure identical heating profiles for each of the vials. The vials were heated to 190° C. and held at that temperature for 2.5 hours, after which the vials were immediately removed from the block heater, quenched in ice water and then analyzed on an Hewlett-Packard ("HP") 6890 GC equipped with a 30 m HP Innowax 0.25 mm diameter column, a HP 5973 mass spectrometer and a flame ionization detector ("FID"). Unconverted MB, unconverted BA and product 3-hydroxypropyl benzoate ("HPB") were measured and results are presented in terms of FID area percents, which correspond to weight percents. Higher activity is reflected by lower levels of reactants MB and BA, and higher levels of HPB. Table 1 shows the initial concentrations of MB, BA and catalyst in each vial and the GC analyses of the final solutions.

Concentrations of Ti, Zr, and TBAH were set by adding specified portions of solutions A, B and C, respectively. Analysis of the solution in vial 2 indicates the extent of conversion possible without a catalyst.

TABLE 1

| | Comparison of Activity of Mixtures Containing Ti, Zr and/or TBAH | | | | | | |
|---|---|---|---|---|---|---|---|
| Run No. | 1 (Comp.) Ti only | 2 (Control) No catalyst | 3 (Comp.) Ti + Zr | 4 (Comp.) Ti + TBAH | 5 (Comp.) Zr + TBAH | Example 6 Ti + Zr + TBAH | 7 (Comp.) Ti + Zr + too much TBAH |
| | Initial Composition | | | | | | |
| BA (wt %) | 3.2 | 3.2 | 3.2 | 3.2 | 3.2 | 3.2 | 3.2 |
| MB (wt %) | 6.0 | 6.0 | 6.1 | 6.3 | 6.2 | 6.2 | 6.1 |
| 3G (wt %) | 90.8 | 90.8 | 90.7 | 90.4 | 90.5 | 90.6 | 90.7 |

TABLE 1-continued

Comparison of Activity of Mixtures Containing Ti, Zr and/or TBAH

| Run No. | 1 (Comp.) Ti only | 2 (Control) No catalyst | 3 (Comp.) Ti + Zr | 4 (Comp.) Ti + TBAH | 5 (Comp.) Zr + TBAH | Example 6 Ti + Zr + TBAH | 7 (Comp.) Ti + Zr + too much TBAH |
|---|---|---|---|---|---|---|---|
| Ti (ppm) | 7.0 | — | 7.7 | 7.1 | — | 7.0 | 7.3 |
| Zr (ppm) | — | — | 6.9 | — | 7.2 | 7.3 | 7.2 |
| TBAH (umol/g) | — | — | — | 0.32 | 0.31 | 0.30 | 0.58 |
| Zr/Ti (mol/mol) | — | — | 0.47 | — | — | 0.55 | 0.52 |
| TBAH/(Ti + Zr) (mol/mol) | — | — | — | 2.2 | 3.9 | 1.3 | 2.5 |
| Final Composition (FID area %) | | | | | | | |
| Unconverted MB | 6.7 | 8.4 | 7.1 | 7.5 | 8.6 | 6.1 | 7.0 |
| Unconverted BA | 4.4 | 4.7 | 4.0 | 4.2 | 4.8 | 3.6 | 4.2 |
| Product HPB | 4.9 | 2.2 | 5.5 | 4.9 | 2.2 | 7.5 | 5.1 |

The composition of the reaction product in comparison run 1, with only Ti as catalyst, shows that the levels of unconverted MB and BA are 6.7% and 4.4%, respectively, and product HPB is 4.9%. In comparison, the use of Zr with Ti in comparison run 3 resulted in slightly better esterification of BA (4.0% with Zr vs 4.4% without) to produce more HPB (5.5% with Zr vs 4.9% without), but the residual concentration of MB is higher (7.1% with Zr vs 6.7% without). This suggests that the addition of Zr to Ti accelerates esterification, but not transesterification. A similar effect is observed when adding TBAH to Ti (comparison run 4). Comparison run 5 using only Zr and TBAH exhibited levels of MB, BA and HPB similar to those of control run 2, without a catalyst, suggesting that the combination of Zr and TBAH provide minimal, if any, catalytic enhancement of reaction rates.

Unexpectedly, the best esterification and transesterification rates are achieved with a mixture of Ti, Zr and TBAH, as shown in run 6. With 7 ppm each of Ti and Zr and 0.3 umol of TBAH as catalyst, reactions of both MB and BA are higher (i.e., less remaining levels of each) resulting in significantly higher levels of HPB. If too much TBAH is added, as in comparison run 7 the synergistic effect of adding Zr and TBAH is negated.

Example 2

A catalyst mixture was prepared as follows. First, 0.2272 g of NPZ was added into a small vial. Then, 0.2574 g of TPT was added and mixed gently, followed by 0.3228 g of 25 weight % tetraethyl ammonium hydroxide in MeOH ("TEAH", City Chemicals Products, West Haven, Conn.). After gentle mixing, 20 cm$^3$ of 3G were added to produce a homogeneous catalyst solution that did not contain any evidence of solids. Other mixtures of Ti, Zr and TEAH were produced in similar fashion. The catalyst solutions were then tested in the same manner as in Example 1, except that total reaction times were reduced to 45 minutes to compensate for the higher levels of catalyst. Results are shown in Table 2.

In addition, a similar solution was prepared with only TPT in 3G and produced a lumpy solution containing white solids.

TABLE 2

Comparison of Activity of Ti, Zr and TEAH Mixtures For Reaction of Methyl Benzoate ("MB") and Benzoic Acid ("BA") with 1,3-Propanediol ("3G")

| Run No. | 1 | 2 | 3 | 4 | 5 | 6 | Comp. 7 |
|---|---|---|---|---|---|---|---|
| Initial Composition | | | | | | | |
| BA (wt %) | 2.9 | 2.9 | 2.7 | 2.9 | 2.9 | 2.9 | 3.0 |
| MB (wt %) | 5.1 | 5.1 | 4.8 | 5.0 | 5.0 | 5.0 | 5.1 |
| 3G (wt %) | 92.0 | 92.0 | 92.4 | 92.1 | 92.1 | 92.1 | 91.9 |
| Ti (ppm) | 59 | 61 | 54 | 60 | 57 | 59 | 55 |
| Zr (ppm) | 60 | 125 | 87 | 62 | 122 | 97 | — |
| TEAH (umol/g) | 0.7 | 0.8 | 0.9 | 1.2 | 1.2 | 0.8 | — |
| Zr/Ti (mol/mol) | 0.53 | 1.1 | 0.85 | 0.54 | 1.1 | 0.86 | — |
| TEAH/(Ti + Zr) (mol/mol) | 0.4 | 0.3 | 0.5 | 0.6 | 0.5 | 0.3 | — |
| Final Composition (FID area %) | | | | | | | |
| Unconverted MB | 6.1 | 6.1 | 5.9 | 6.1 | 6.0 | 6.0 | 6.7 |
| Unconverted BA | 3.5 | 3.6 | 3.5 | 3.5 | 3.4 | 3.5 | 4.0 |
| Product HPB | 3.9 | 4.2 | 3.7 | 4.0 | 4.3 | 4.2 | 2.5 |

For the each of the Ti, Zr and TEAH catalyst mixtures in vials 1 to 6, higher rates of reaction (lower levels of unreacted MB and BA and higher levels of product HPB) are observed in comparison with comparison run 7 in which only Ti was used as a catalyst. The highest levels of HPB are produced when using a Zr/Ti molar ratio greater than 0.5:1 and with molar TEAH ratios (molar ratio of TEAH/(moles of Ti+Zr)) as low as 0.3:1.

Example 3

Catalyst mixtures were prepared in the same manner as in Example 2, but using TBAH, TEAH, or tetramethyl ammonium hydroxide ("TMAH" as 25% TMAH in methanol, City Chemicals Products) as the tetraalkyl ammonium hydroxide ("TAAH") component. Results in Table 3 show the catalytic effect of the various mixtures.

TABLE 3

Activity of Ti, Zr and TetraAlkyl Ammonium Hydroxide ("TAAH")
Mixtures For Reaction of MB and BA with 1,3-Propanediol ("3G")

| Run No. | 1 | 2 | 3 | Comp. 4 | 5 | 6 | 7 |
|---|---|---|---|---|---|---|---|
| Initial Composition | | | | | | | |
| TAAH | TEAH | TMAH | TBAH | — | TEAH | TMAH | TBAH |
| BA (wt %) | 2.9 | 2.9 | 2.9 | 2.9 | 2.9 | 2.8 | 2.9 |
| MB (wt %) | 5.0 | 5.2 | 5.0 | 5.1 | 4.8 | 4.7 | 5.0 |
| 3G (wt %) | 92.1 | 92.0 | 92.1 | 92.0 | 92.3 | 92.5 | 92.1 |
| Ti (ppm) | 59 | 60 | 59 | 55 | 60 | 56 | 59 |
| Zr (ppm) | 96 | 99 | 99 | — | 98 | 92 | 100 |
| TAAH (umol/g) | 0.8 | 0.8 | 0.8 | — | 0.8 | 0.7 | 0.8 |
| Zr/Ti (mol/mol) | 0.85 | 0.87 | 0.88 | — | 0.86 | 0.86 | 0.89 |
| TAAH/(Ti + Zr) (mol/mol) | 0.3 | 0.3 | 0.3 | — | 0.3 | 0.3 | 0.3 |
| Final Composition (FID area %) | | | | | | | |
| Unconverted MB | 5.9 | 6.1 | 5.9 | 6.6 | 5.5 | 5.6 | 6.0 |
| Unconverted BA | 3.7 | 3.7 | 3.8 | 4.3 | 3.8 | 3.7 | 3.9 |
| Product HPB | 4.0 | 4.1 | 4.1 | 2.5 | 4.2 | 3.8 | 4.1 |

The product compositions indicate that catalyst mixtures composed of any of the tetraalkyl ammonium hydroxides exhibit excellent activity when present in the same molar proportions. In each case, the activity of the mixture is higher than the activity of the comparable solution containing TPT alone.

Comparative Example 4

This comparative example shows a batch preparation of poly(trimethylene terephthalate) ("3GT") using TPA, 3G and TPT.

First, 10.2 g of TPT was mixed with ~300 g of 3G. This formed a yellow mixture containing some solid white agglomerates which were somewhat broken up by vigorous mixing. This mixture was added to 75 pounds (34 kg) of 3G and 102 pounds (46.3 kg) of TPA (Amoco purified TPA) in a well-stirred vessel. The vessel was purged with $N_2$, pressurized to 50 psig and then heated to a final batch temperature of 245° C. $H_2O$ was continually drawn off through a column mounted above the vessel. Oligomer in the vessel became clear after 395 minutes, after which the vessel was depressurized. After the vessel was depressurized to 5 psig, the oligomer was transferred to an autoclave reactor where an additional 10.2 g of TPT (mixed in ~300 g of 3G) were added. The autoclave pressure was slowly ramped from atmospheric pressure to a pressure below 1 mm Hg in 1 hour and the temperature was ramped to 255° C. Oligomer was continuously agitated at a speed of 25 rpm for a period of 225 total minutes in the autoclave reactor from the beginning of the pressure letdown cycle. 3GT with an IV of approximately 0.8 dl/g was produced with color properties as listed in Table 4.

Example 5

This example demonstrates a batch preparation of 3GT using TPA, 3G and the catalyst of the invention.

13.2 g of NPZ, 10.2 g of TPT and 12.6 g of 25% TEAH in MeOH (City Chemicals Products) (Zr/Ti=0.79 mol/mol, TEAH/(Zr+Ti)=0.33 mol/mol) were mixed together and ~100 g of 3G was added to produce a clear, slightly yellow, homogeneous catalyst solution. The catalyst was added to 75 pounds (34 kg) of 3G and 102 pounds (46.3 kg) of TPA in a well-stirred vessel. The vessel was purged, pressurized to 50 psig and heated to a final batch temperature of 243° C. Oligomer in the vessel became clear after 335 minutes, after which the vessel was depressurized.

In contrast to Comparative Example 4, the enhanced catalytic effect of the catalyst of this invention is evident in the reduced time of approximately 1 hour required for esterification.

After transferring the oligomer into the autoclave, an additional mixture of 13.2 g of NPZ, 10.2 g of TPT and 12.6 g of TEAH (Zr/Ti=0.79 mol/mol, TEAH/(Zr+Ti)=0.33 mol/mol) was added. The polymerization procedure used in Comparative Example 4 was followed. The total time in the autoclave was approximately 243 minutes from the beginning of the pressure letdown cycle. 3GT with an IV of approximately 0.8 dl/g was produced with color properties as listed in Table 4.

Example 6

This example shows a batch preparation of 3GT polymer using TPA, 3G and the catalyst of the invention.

6.6 g of NPZ, 5.1 g of TPT, and 3.9 g of 25% tetramethyl ammonium hydroxide ("TMAH") in MeOH (City Chemicals Products) (Zr/Ti=0.79 mol/mol, TEAH/(Zr+Ti)=0.33 mol/mol) were mixed together and ~100 g of 3G was added to produce a clear, colorless, homogeneous catalyst solution. The catalyst was added to 75 pounds (34 kg) of 3G and 102 pounds (46.3 kg) of TPA in a well-stirred vessel. The vessel was purged, pressurized to 50 psig and heated to a final batch temperature of 233° C. Oligomer in the vessel became clear after 390 minutes, after which the vessel was depressurized. Comparing with Comparative Example 4, the esterification time is comparable despite requiring only half the amount of TPT. This shows that the activity level increased per mass of Ti.

After transferring the oligomer into the autoclave, an additional mixture of 13.2 g of NPZ, 10.2 g of TPT and 7.8 g of 25% TMAH (Zr/Ti=0.79 mol/mol, TEAH/(Zr+Ti)=0.33 mol/mol) was added. The polymerization procedure used in Comparative Example 4 was followed. The total time in the autoclave was approximately 261 minutes from the beginning of the pressure letdown cycle. 3GT with an IV of approximately 0.8 dl/g was produced with color properties as listed in Table 4.

TABLE 4

Polymer Color of Batch 3GT Polymers Produced from TPA (Measurements made Using a Varian Cary 5 uv/vis/nir spectrophotometer)

|  | Comp. Ex. 4 | Example 5 | Example 6 |
|---|---|---|---|
| L | 79.7118 | 79.474 | 82.678 |
| a* | −0.695 | −1.059 | −0.744 |
| b* | 1.936 | −0.251 | 0.795 |

Table 4 shows the improvement (i.e., decrease) in b* color of the batch 3GT polymers prepared using the catalyst of the invention in Examples 5 and 6. In all cases, polycondensation was carried out to achieve approximately the same agitator torque, resulting in polymer IV's of about 0.8 dl/g in each case.

Comparative Example 7

This example shows a batch preparation of 3GT using DMT, 3G and TPT.

18.0 g of TPT was mixed with ~300 g of 3G. The TPT catalyst mixture was added to 60 pounds (27.2 kg) of 3G and 120 pounds (54.4 kg) of DMT in a well-stirred vessel that was equipped on top with a column. Product methanol was withdrawn through the top of the column. The vessel was jacketed with hot oil that was initially heated to 200° C. 30 minutes after the beginning of methanol production, the oil temperature was raised by 5° C. Each 30 minutes thereafter, the oil temperature was increased in 5° C. increments until the stoichiometric amount of methanol was produced. Approximately 225 minutes after the beginning of methanol generation, the oligomer was transferred into an autoclave reactor for polymerization.

The autoclave pressure was ramped from atmospheric pressure to a pressure below 1 mm Hg in 1 hour and the temperature was ramped to 255° C. Oligomer was continuously agitated at a speed of 25 rpm until a specified torque was achieved. This resulted in 3GT with an IV of about 0.8 dl/g.

Example 8

This example demonstrates batch preparation of 3GT using DMT, 3G and the catalyst of the invention, and shows the shorter transesterification time obtained using the catalyst of the invention.

22.0 g of NPZ, 17.0 g of TPT and 13.0 g of TMAH (Zr/Ti=0.79 mol/mol, TEAH/(Zr+Ti)=0.33 mol/mol) were mixed together with 100 g of 3G to form a clear, colorless, liquid solution. This solution was added to 60 pounds (27.2 kg) of 3G and 120 pounds (54.4 kg) of DMT in a well-stirred vessel. The vessel was heated using the same temperature program as described in Comparative Example 7. Approximately 200 minutes after the beginning of methanol generation, the oligomer was transferred into an autoclave reactor for polymerization. With the catalyst of the invention, the transesterification time is shortened and it has also been observed that transesterification initiates at lower temperatures as compared with TPT alone.

The autoclave pressure was ramped from atmospheric pressure to a pressure below 1 mm Hg in 1 hour and the temperature was ramped to 255° C. Oligomer was continuously agitated at a speed of 25 rpm until a specified torque was achieved, resulting in a polymer with an IV of about 0.8 dl/g.

Figure 1:
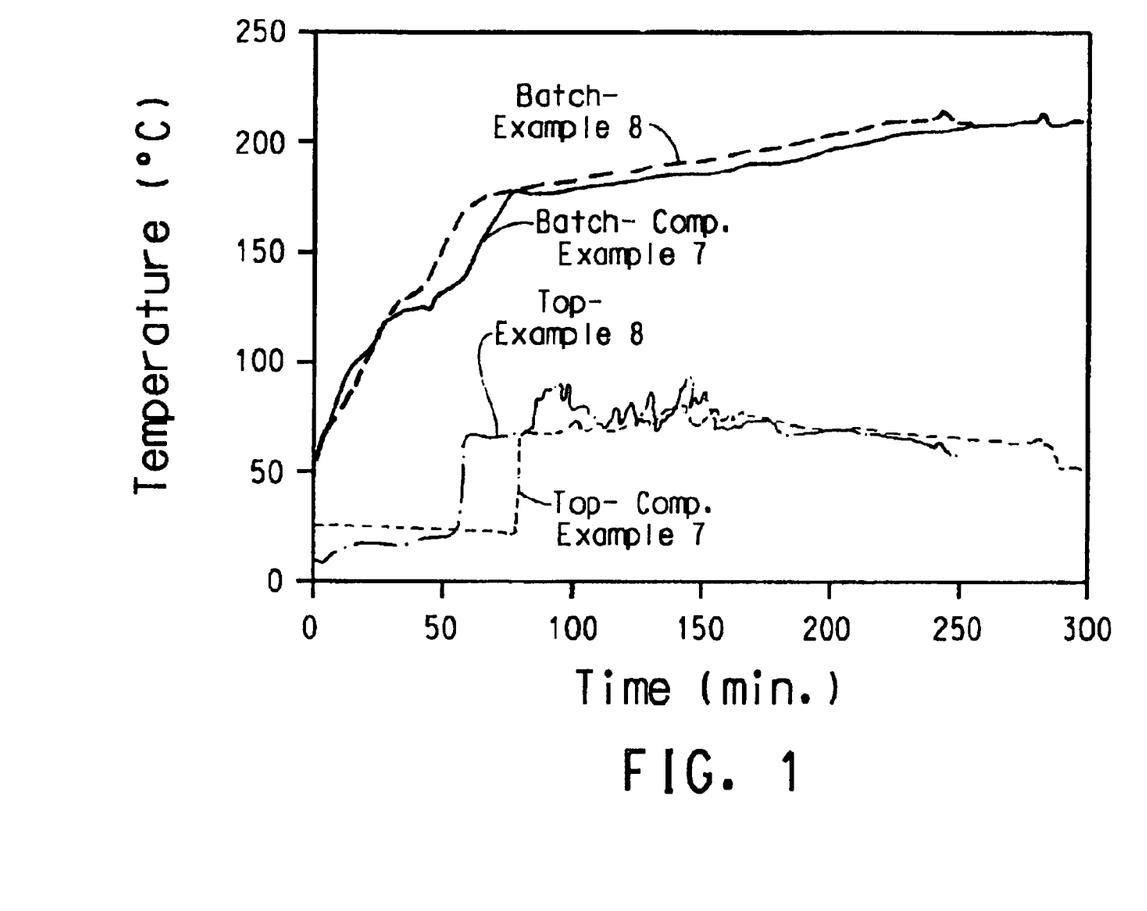

FIG. 1 compares the batch oligomer temperature and top of column temperature profiles during transesterification for Comparative Example 7 and Example 8. The bottom two lines indicate the temperatures at the top of the column. Thus, the point at which the temperature first increases corresponds to when methanol generation begins and the point at which the temperature decreases indicates when transesterification is complete. The graph shows that methanol was generated earlier when using the catalyst of the invention. That is, the earlier rise in the line for the reaction carried out with the catalyst of the invention shows that methanol is being generated earlier. The top two lines of the graph show the temperature profile within the reactor. The lines end when the reaction were completed, and it can be seen that the reaction was completed faster with the catalyst of the invention. Thus, FIG. 1 shows that the reaction was initiated and completed more quickly with the catalyst of the invention.

Comparative Example 9

A stream of 75.4 pounds (34.2 kg)/hour DMT was preheated to 185° C. and mixed with a stream of 53.2 pounds (24.1 kg)/hour 3G preheated to 185° C. and 0.0237 pounds (10.75 g)/hour TPT (50 ppm Ti). The mixed feed was injected into the calandria of an ester exchanger that was controlled to a temperature of approximately 230° C. and a pressure between 900 and 950 mm Hg. The oligomer produced was polymerized through a flasher, prepolymerizer and finisher, as described in WO 01/58981.

Comparative Example 10

A stream of 75.4 pounds (34.2 kg)/hour DMT was preheated to 185° C. and injected into the 16$^{th}$ tray of the ester exchanger column. A stream of 53.2 pounds (24.1 kg)/hour 3G and 0.0237 pounds (10.75 g)/hour TPT (50 ppm Ti) was preheated to 185° C. and injected into the 17$^{th}$ tray of the ester exchanger column. An additional 6.0 pounds (2.7 kg)/hour 3G was injected into the calandria. The ester exchanger calandria temperature was maintained at approximately 255° C. and a pressure of approximately 950 mm Hg. The oligomer produced was polymerized through a flasher, prepolymerizer and finisher, as described in WO 01/58981.

Example 11

A stream of 75.4 pounds (34.2 kg)/hour DMT was preheated to 185° C. and injected into the 16$^{th}$ tray of the ester exchanger column. A stream containing 53.2 pounds (24.1 kg)/hour 3G, 0.0119 pounds (5.4 g)/hour TPT (25 ppm Ti), 0.0102 pounds (4.6 g)/hour Tyzor NPZ, and 0.0070 pounds (3.2 g)/hour 25% TMAH in MeOH (Zr/Ti=0.53 mol/mol, TMAH/(Zr+Ti)=0.30) was preheated to 185° C. and injected into the 17$^{th}$ tray of the ester exchanger column. An additional 6.0 pounds (2.7 kg)/hour 3G was injected into the calandria. The ester exchanger calandria temperature was maintained at approximately 249° C. and a pressure of approximately 950 mm Hg. The oligomer produced was polymerized through a flasher, prepolymerizer and finisher, as described in WO 01/58981.

Random samples of polymers produced in Comparative Examples 9 and 10 and Example 11 were crystallized at 100° C. Samples of amorphous and crystallized polymer pellets were analyzed for color (Table 5). Data in Table 5 indicates that the catalyst of the invention added in amount of 25 ppm Ti is capable of producing polymer of comparable viscosity to 50 ppm Ti in TPT (LRV's ranged between 40 and 45 throughout Comparative Examples 9 and 10 and Example 11). Comparing colors of amorphous polymers indicates that using the catalyst of the invention results in lower b colors. This is consistent with the b colors of the crystallized polymers. Thus, the color of the polymers produced with the catalyst of the invention was more than 3 b units better than that of the polymers prepared using TPT only.

TABLE 5

LRV and Color of Polymers Prepared in Comparative Examples 9 and 10 and Example 11
(Color Measurements made using Hunterlab LabScan XE)

|  | Comparative Example 9 | | | Comparative Example 10 | Example 11 |
|---|---|---|---|---|---|
| Catalyst (ppm Ti) | 50 | 50 | 50 | 50 | 25 |
| LRV | 42.0 | 40.6 | 42.3 | 44.1 | 39.9 |
| b-amorphous | 12.3 | 13.5 | 14.3 | 16.4 | 10.3 |
| L-crystal | 82.2 | 82.7 | 81.4 | 80.8 | 79.7 |
| a-crystal | −2.4 | −2.5 | −2.6 | −3.6 | −2.1 |
| b-crystal | 9.1 | 9.7 | 10.1 | 11.7 | 5.9 |

Comparative Examples 12 and 13 and Example 14

This example shows continuous esterification of TPA with 3G and TPT.

A paste feed containing approximately 50 pounds (22.7 kg)/hour TPA and 3G in a molar ratio of approximately 2.1 was continuously fed into a circulating esterification reactor designed after U.S. Pat. No. 3,927,982. $H_2O$ and 3G vapors were continuously taken off and separated in a column. 3G vapors condensed from the column were collected in a recycle tank from which 3G was refluxed back into the top of the esterification reactor at a rate of about 97 pounds (44 kg)/hour (4.23G/TPA mole ratio). Including reflux, the total molar 3G/TPA feed to the reactor was 6.3. TPT catalyst was initially added to the paste at a rate equivalent to 50 ppm Ti relative to final polymer. Oligomer exiting the esterification reactor was sampled approximately every 4 hours into a sealed cylinder. Oligomer samples were dissolved in heated o-cresol. Residual carboxyl ends were measured by titration using a 0.005 N KOH in methanol solution.

At time 0–30 hours, 50 ppm of Ti in the form of TPT (Comparative Example 12) is added as an esterification catalyst resulting in oligomer carboxyl levels of about 75 meq/kg. As the concentration of TPT catalyst is reduced to 30 ppm Ti (Comparative Example 13), the lower catalytic activity causes the oligomer carboxyl levels to rise to approximately 150 meq/kg. Conversely, with the same level of Ti (30 ppm), but the catalyst of this invention, oligomer carboxyl levels decrease to approximately 75 meq/kg. In view of the higher activity of the catalyst of this invention, only 15 ppm Ti is required to produce oligomer carboxyl levels in the range of 150 meq/kg. Thus, the catalyst of this invention exhibits higher esterification activity per mass of Ti than that of a comparison TPT catalyst.

Figure 2:
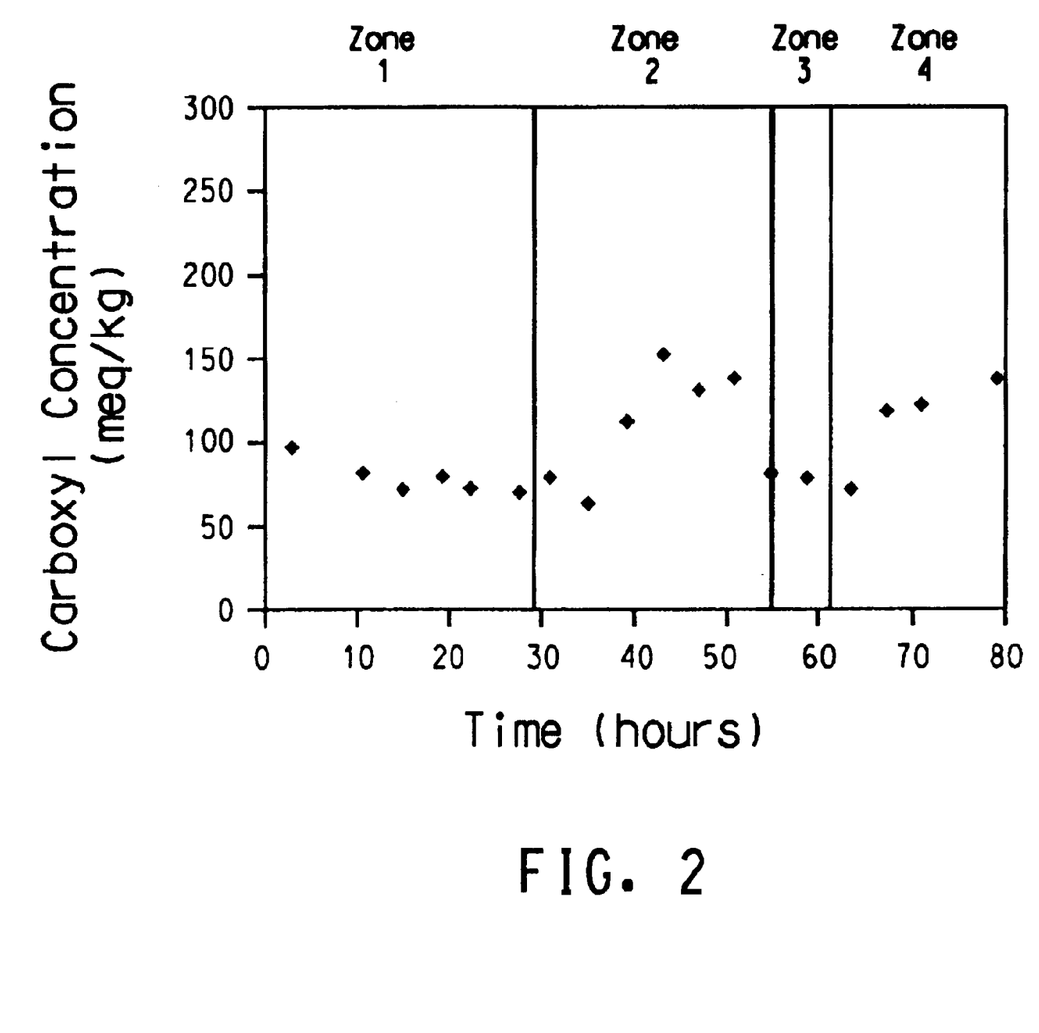
FIG. 2 shows the effect of varying catalyst type and level on residual oligomer carboxyl ends concentration in continuous terephthalic acid esterification with 1,3-propanediol in Example 14 and Comparative Examples 12 and 13.

As shown in FIG. 2, Zone 1, the residual carboxyl ends in the oligomer when using 50 ppm Ti (from TPT) as catalyst is approximately 75 meq/kg. As can be seen in Zone 2, when the TPT level is decreased to 30 ppm Ti, the residual carboxyl ends increases to about 140 meq/kg, reflecting the lower activity associated with 40% less catalyst.

After approximately 55 hours, the catalyst was changed to the catalyst of the invention at a level of 30 ppm Ti (Zr/Ti=0.79 mol/mol, TEAH/(Ti+Zr)=0.33) (Example 14). As can be seen in Zone 3, despite the same level of Ti, the catalyst of the invention caused the residual carboxyl ends to decrease to about 75 meq/kg. As can be seen in Zone 4, when the catalyst of the invention's level was decreased to 15 ppm Ti (Zr/Ti=0.79 mol/mol, TEAH/(Ti+Zr)=0.33), the carboxyl ends increased to about 140 meq/kg.

The amount of carboxyl end groups is inversely related to catalyst activity. Thus, a faster reaction can be demonstrated by the carboxyls reacting and there being a lower carboxyl concentration. Therefore, FIG. 2 shows that the reaction using the invention at 30 ppm Ti was at least as fast as a TPT catalyzed reaction at 50 ppm Ti. In addition, at 15 ppm Ti the reaction with catalyst of the invention was faster than the reaction carried out using 30 ppm Ti.

After exiting the esterifier, an additional 30 ppm Ti as TPT was continuously added to the oligomers prepared in Comparative Examples 12 and 13 (TPT at 50 ppm and 30 ppm, respectively) and polymerized through a flasher, prepolymerizer and finisher, as described in WO 01/58981.

30 ppm Ti as part of the catalyst of the invention (Zr/Ti=0.79 mol/mol, TEAH/(Zr+Ti)=0.33 mol/mol) was continuously added to the oligomer prepared in Example 12 and polymerized through a flasher, prepolymerizer and finisher, as described in WO 01/58981.

Random samples of polymers produced in Comparative Examples 12, 13 and Example 14 were analyzed to show the properties listed in Table 6. Color analyses of the polymers shown in Table 6 indicate that the catalyst of the invention results in desirable lower b colors.

TABLE 6

LRV and b Color of Sample Polymers Produced in Comparative Examples 12, 13 and Example 14
(Measurements made using Hunterlab LabScan XE)

|  | Comparative Example 12 | Comparative Example 13 | Example 14 |
|---|---|---|---|
| LRV | 49.2 | 49.0 | 36.4 |
| B color | 13.1 | 12.6 | 8.3 |

Example 15

A catalyst mixture was prepared using ethylene glycol. 0.9949 g of Tyzor TPT was added to 1.3021 g of Tyzor NPZ and gently mixed. 0.7636 g of 25% TMAH in methanol was added and mixed, followed by 13.7928 g of ethylene glycol to form a uniform 1 wt % Ti (Zr:Ti=1.5:1, TMAH:(Zr+Ti)=0.33:1) in ethylene glycol mixture. A homogeneous solution resulted.

Example 16

A catalyst mixture was prepared using 1,4-butanediol.

2.038 g of Tyzor TPT was added to 2.6014 g of Tyzor NPZ and gently mixed. 1.5727 g of 25% TMAH in methanol was added and mixed, followed by 10.9806 g of 1,4-butanediol to form a uniform 2 wt % Ti (Zr:Ti=3.0:1, TMAH:(Zr+Ti)=0.48:1) in 1,4-butanediol. A homogeneous solution resulted.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the disclosure.

What is claimed is:

1. A catalyst composition prepared from (a) titanium tetrahydrocarbonyloxide, (b) zirocnium tetrahydrocarbyloxide, and (c) tetraalkyl ammonium hydroxide (TAAH), wherein the molar ratio of Zr:Ti is from about 0.02:1 to about 5:1 and the molar ratio of TAAH:(Ti+Zr) is from about 0.05:1 to about 2:1, and does not contain phosphorus or a phosphorus compound.

2. The catalysts composition of claim 1 wherein the titanium tetrahydrocarbyloxide is tetraalkyl titanate.

3. The catalysts composition of claim 1 wherein the zirconium tetrahydrocarbyloxide is tetraalkyl zirconate.

4. The catalysts composition of claim 1 wherein the tetraalkyl ammonium hydroxide is selected from the group consisting of tetraalkyl ammonium hydroxides with alkyl groups containing 1–20 carbon atoms, which can be the same or different, and combinations thereof.

5. A catalyst mixture comprising the catalyst composition of claim 1 and glycol.

6. The catalyst mixture of claim 5 wherein the glycol is a $C_2$ to $C_{12}$ glycol.

7. The catalyst mixture of claim 5 wherein the glycol is selected from the group consisting of ethylene glycol, 1,2-propanediol, 1,3-propanediol and 1,4-butanediol, and mixtures thereof.

8. The catalyst mixture of claim 5 wherein the glycol is 1,3-propanediol.

9. The catalyst mixture of claim 5 wherein the glycol is ethylene glycol.

10. The catalyst mixture of claim 5 wherein the glycol is 1,4-butanediol.

11. A process of producing a polyester comprising [i] esterifying or transesterifying (a) organic acid, or ester or salt of an organic acid, and (b) alcohol to form an intermediate reaction product, and [ii] polycondensing the intermediate reaction product to form polyester, wherein the catalyst composition of claim 1 catalyzes the esterifying, transesterifying or polycondensing.

12. The process of claim 11 wherein the polyester is poly(trimethylene terephthalate).

13. A catalyst composition prepared from (a) tetraalkyl titanate, (b) tetraalkyl zirconate, and (c) tetraalkyl ammonium hydroxide (TAAH), wherein the molar ratio of Zr:Ti is from about 0.02:1 to about 5:1 and the molar ratio of TAAH:(Ti+Zr) is from about 5:1 to about 2:1, and does not contain phosphorus or a phosphorus compound.

14. The catalyst composition of claim 13 wherein the molar ratio of Zr:Ti is 0.1:1 to 3:1.

15. The catalyst composition of claim 13 wherein the molar ratio of Zr:Ti is 0.1:1 to 1:1.

16. The catalyst composition of claim 13 wherein the molar ratio of TAAH:(Ti+Zr) is 0.05:1 to 1:1.

17. The catalyst composition of claim 13 wherein the molar ratio of TAAH:(Ti+Zr) is 0.1:1 to 0.5:1.

18. The catalyst composition of claim 13 wherein the tetraalkyl titanate is selected from those having the general formula $Ti(OR)_4$ where each R is independently selected from the group consisting of an alkyl radical, a cycloalkyl radical, an aralkyl hydrocarbon radical containing from 1 to 30 carbon atoms, and combinations thereof.

19. The catalyst composition of the claim 13 wherein tetraalkyl titanate is selected from the group consisting of titanium tetraethoxide, titanium tetrapropoxide, titanium tetrahexoxide, titanium tetra 2-ethylhexoxide, titanium tetraoctoxide, titanium tetraisopropoxide and titanium tetra-n-butoxide and combinations thereof.

20. The catalyst composition of claim 13 wherein the tetraalkyl zirconate is selected from tetraalkyl zirconates having the general formula $Zr(OR^1)_4$ where each $R^1$ can be the same or different and is a hydrocarbyl radical having 1 to about 10 carbon atoms per radical, and combinations thereof.

21. The catalyst composition of claim 13 wherein the tetraalkyl zirconate is selected from the group consisting of tetra n-propyl zirconate, tetra n-butyl zirconate, and combinations thereof.

22. The catalyst composition of claim 13 wherein the tetraalkyl ammonium hydroxide is selected from the group consisting of tetraalkyl ammonium hydroxides with alkyl groups containing 1–10 carbon atoms and combinations thereof.

23. The catalyst composition of claim 13 wherein the tetraalkyl ammonium hydroxide selected from the group consisting of tetra methyl, ethyl, propyl and butyl ammonium hydroxide, choline hydroxide, (trimethyl(2-hydroxyethyl)ammonium hydroxide), benzyltrimethyl ammonium hydroxide, and combinations thereof.

24. The catalyst composition of claim 13 wherein the tetraalkyl titanate is selected from those having the general formula $Ti(OR)_4$ where each R is independently selected from alkyl radicals with 2 to 12 carbon atoms per radical and combinations thereof; the tetraalkyl zirconate is selected from the group having the general formula $Zr(OR^1)_4$ where each $R^1$ is independently selected from an alkyl radical having 1 to 10 carbon atoms and combinations thereof; and the tetraalkyl ammonium hydroxide is selected from the group consisting of tetraalkyl ammonium hydroxides with alkyl groups containing 1–10 carbon atoms, which can be the same or different, and mixtures thereof, and wherein the molar ratio of Zr:Ti is 0.1:1 to 1:1 and the molar ratio of TAAH:(Ti+Zr) is 0.1:1 to 0.5:1.

25. A catalyst composition consisting essentially of the product of mixing (a) tetraalkyl titanate, (b) tetraalkyl zirconate, and (c) tetraalkyl ammonium hydroxide (TAAH), wherein the molar ratio of Zr:Ti is from about 0.02:1 to about 5:1 and the molar ratio of TAAH:(Ti+Zr) is from about 0.05:1 to about 2:1.

* * * * *

UNITED STATES PATENT AND TRADEMARK OFFICE
CERTIFICATE OF CORRECTION

PATENT NO. : 6,841,505 B2
DATED : January 11, 2005
INVENTOR(S) : Eng

It is certified that error appears in the above-identified patent and that said Letters Patent is hereby corrected as shown below:

Column 19,
Line 3, please replace "zirocnium" with -- zirconium --

Signed and Sealed this

Ninth Day of August, 2005

JON W. DUDAS
*Director of the United States Patent and Trademark Office*